United States Patent [19]

Winston

[11] Patent Number: 5,425,952
[45] Date of Patent: Jun. 20, 1995

[54] SLOW-RELEASE AMMONIUM BICARBONATE FUNGICIDE COMPOSITIONS

[75] Inventor: Anthony E. Winston, East Brunswick, N.J.

[73] Assignee: Church & Dwight Co., Inc., Princeton, N.J.

[21] Appl. No.: 136,388

[22] Filed: Oct. 13, 1993

[51] Int. Cl.$^6$ ............ A01N 59/00; A01N 25/00; A01N 25/24; A01N 37/18
[52] U.S. Cl. .................... 424/717; 514/143; 514/241; 514/476; 514/491; 514/547; 514/553; 514/557; 514/558; 514/560; 514/578; 514/579; 514/588; 514/591; 514/594; 514/613; 514/709; 514/710; 514/711; 514/762; 514/772; 514/772.3; 514/777; 514/778; 514/780; 514/781; 514/782; 514/786; 514/789; 424/78.08; 424/405; 424/407; 424/484; 424/715; 424/716; 424/719; 424/721
[58] Field of Search ............ 424/715, 716, 717, 78.08, 424/405, 407, 484, 719, 721; 514/143, 241, 476, 491, 547, 553, 557, 558, 560, 578, 579, 588, 591, 594, 613, 709, 710, 711, 762, 772, 772.3, 777, 778, 780, 781, 782, 786, 789

[56] References Cited

U.S. PATENT DOCUMENTS 1,047,592  12/1912  Thomas ............................ 424/716
4,599,233   7/1986  Misato et al. .................... 424/717

FOREIGN PATENT DOCUMENTS 53-96319   8/1978  Japan .
60-153785  8/1985  Japan .

OTHER PUBLICATIONS

DePasquale, "Antifungal activities of bicarbonate salts with particular emphasis on the ammonium form," University Microfilms International, MI, 1990, pp. 1-108.

*Primary Examiner*—Allen J. Robinson
*Assistant Examiner*—John D. Pak
*Attorney, Agent, or Firm*—Charles B. Barris

[57] ABSTRACT

This invention provides a fungicide composition which is capable of in situ generation of ammonium bicarbonate when applied to plant foliage in the form of an aqueous dispersion. The constituents include (1) an ingredient such as urea which slow-releases ammonia under aqueous alkaline pH conditions; and (2) an alkali metal bicarbonate ingredient which imparts alkalinity to the aqueous dispersion, and provides bicarbonate ions for combination with the released ammonium ions. A spreader-sticker ingredient is included to maintain the ingredients in contact with plant foliage over an extended period after application.

22 Claims, No Drawings

SLOW-RELEASE AMMONIUM BICARBONATE FUNGICIDE COMPOSITIONS

BACKGROUND OF THE INVENTION

The control of phytopathogenic fungi is of great economic importance since fungal growth on plants or on parts of plants inhibits production of foliage, fruit or seed, and diminishes the overall quality of a cultivated crop.

Because of the vast economic ramifications of fungal propagation in agricultural and horticultural cultivations, a broad spectrum of fungicidal and fungistatic products have been developed for general and specific applications.

Of particular interest with respect to the present invention embodiments are fungicide compositions which contain an inorganic bicarbonate or carbonate compound. It is known that bicarbonate and carbonate compounds exhibit fungicidal properties for agricultural purposes.

Phytopathology, 48, 169 (1931) by R. H. Marloth describes studies involving the physiology of fungi. The reference reports studies which demonstrate that sodium and potassium bicarbonate and carbonate salts are toxic to fungi such as *Penicillum italicum* and *Penicillum digitalum*.

U.S. Pat. No. 1,560,558 discloses the use of salts such as lithium carbonate, sodium carbonate, sodium bicarbonate, potassium bicarbonate, potassium carbonate and ammonium bicarbonate as fungicide ingredients.

U.S. Pat. No. 4,599,233 describes a fungicide composition which consists of sodium bicarbonate in combination with a surface active food emulsifier such as sorbitan monostearate.

Japanese patent 53096319 describes the application of potassium bicarbonate as an active biocide for the control of fungal diseases common to tomato and cucumber plants.

Japanese patent 56043207 describes a biocidal composition containing sodium bicarbonate and a polyglycerol fatty acid ester. The biocide controls *Penicillum digitatum* on oranges, *Sphaerotheca fuligenea* on cucumbers, *Piricularia oryzae* on rice, and mosaic virus on tomatoes.

Japanese patent 60097909 describes a soil fungicide prepared by admixing slaked lime with sodium bicarbonate, potassium bicarbonate, boric acid and phenolphthalein.

Japanese patent 57062208 describes horticultural fungicides in which the addition of sodium bicarbonate to polyoxin or thiophanatemethyl increases the fungicidal activity of the organic biocide against *botrytis cinerea* on cucumbers.

Japanese patent 58023609 describes an agricultural fungicide composed of a mixture of sodium bicarbonate or potassium bicarbonate with cupric hydroxide, basic copper carbonate or basic copper sulfate. The combination of ingredients exhibits a synergistic fungicidal effect against cucumber early blight, tomato wilt, rice sheath blight, rice blast and citrus canker.

While the fungicidal activities of alkali metal bicarbonates are well-established, there is less certainty concerning the fungicidal activity of the related ammonium bicarbonate. In vitro studies indicate that ammonium bicarbonate often is more effective than sodium or potassium bicarbonate for control of fungus growth. In contradistinction, in vivo application of ammonium bicarbonate generally is not effective for control of foliar fungi. Sodium and potassium bicarbonate but not ammonium bicarbonate are effective for controlling powdery mildew on roses. However, ammonium bicarbonate is efficacious for control of soil fungi such as *Sclerotinia sclerotiorum* infection of peanut crops.

It appears that ammonium bicarbonate is less effective in plant foliar applications for fungus control because ammonium bicarbonate is less stable than alkali metal bicarbonate under ambient temperature and moisture conditions. The ammonium bicarbonate does not remain intact as an active biocidal entity for a sustained duration and in a sufficient contact concentration to achieve fungus control.

There is a continuing interest in the development of new and more effective fungicides which possess preventive, curative and systemic activity for the protection of cultivated plants, with a minimum of phytotoxic side effects.

Accordingly, it is an object of this invention to provide a dry blend biocide composition which releases at least two bicarbonate ingredients exhibiting fungicidal properties when applied to agricultural and horticultural plants as a powder, an aqueous dispersion, or a solution.

It is another object of this invention to provide a fungicide composition which is an aqueous formulation of ingredients adapted for sustained in situ generation of ammonium bicarbonate when applied to plant foliage.

Other objects and advantages of the present invention shall become apparent from the accompanying description and examples.

DESCRIPTION OF THE INVENTION

One or more objects of the present invention are accomplished by the provision of a fungicide composition consisting of a dry blend formulation adapted for in situ generation of ammonium bicarbonate which comprises (1) between about 5-80 weight percent of an ingredient selected from water-soluble organic amides which slow-release ammonia under aqueous alkaline pH conditions at ambient temperatures; (2) between about 10-80 weight percent of an ingredient selected from alkali metal bicarbonates; (3) between about 0-30 weight percent of an ingredient selected from alkali metal and ammonium carbonates; and (4) between about 0.5-20 weight percent of a spreader-sticker ingredient; based on the composition weight.

An invention dry blend fungicide composition can be in the form of dusting powders, which optionally can include a solid diluent such as bentonite, calcium carbonate, magnesia, gypsum, kieselguhr, diatomaceous earth, and the like. Plant foliage can be treated with a dusting powder, and ambient weather cycles and atmospheric conditions provide sufficient moisture to convert the applied dusting powder to an adherent coating on the plant foliage. A dusting powder preferably has an average particle size diameter between about 1-100 microns, and has a content of submicron particles.

A dry blend fungicide composition also can be diluted with water to form aqueous fungicidal solutions with controlled rheological properties. An aqueous fungicidal solution typically contains less than about 5 weight percent of active ingredients, based on the solution weight. For most applications the content of bicarbonate ingredient is maintained at a concentration below about one weight percent, as a means of minimizing phytotoxic effects on treated plants which are sensitive to alkaline pH conditions.

In another embodiment this invention provides an aqueous fungicidal formulation adapted for in situ generation of ammonium bicarbonate under cultivated plant application conditions, which contains ingredients comprising (1) between about 0.1–5 weight percent of water-soluble organic amide which slow-releases ammonia under aqueous alkaline pH conditions at ambient temperature; (2) between about 0.2–5 weight percent of alkali metal bicarbonate; (3) between about 0–2 weight percent of alkali metal or ammonium carbonate; and (4) between about 0.02–1.5 weight percent of a spreader-sticker ingredient; based on the formulation weight.

A preferred aqueous formulation has a carbonate salt content between about 0.1–1 weight percent.

In another embodiment this invention provides a method of controlling fungal disease in cultivated plants which comprises applying a present invention fungicide composition to the plant foliage to prevent or eradicate fungal infections.

The term "water-soluble" as employed herein refers to an organic amide which has a solubility of at least about 0.5 gram per 100 grams of water at 25° C.

Illustrative of water-soluble organic amides which slow-release ammonia in accordance with the present invention are urea; urea-formaldehyde adducts such as monomethyloeurea and dimethyloeurea; urea hydrochloride; urea nitrate; urea phosphate; alkali metal carbamate; biuret; triuret; cyanuric acid; and the like.

A urea ingredient also can be included in the form of a crystalline urea clathrate complex, which contains an occluded long chain compound which can exhibit spreader-sticker properties on foliage surfaces. In an aqueous medium the clathrate complex dissociates, and the urea and long chain compound function as separate molecules. The occluded long chain compound can be an anionic, cationic or nonionic surfactant, or a paraffinic type spray oil used in crop applications.

Illustrative of a crystalline clathrate is a combination of urea with an ethoxylated $C_{12}$–$C_{15}$ alcohol containing an average of 7 moles of ethylene oxide. The clathrate is prepared by heating a mixture of one part alcohol and 5 parts urea to 150° C. to form a melt, and then cooling the liquid mixture to yield a crystalline clathrate complex of the two compounds.

The bicarbonate salt ingredient of an invention fungicide composition is sodium bicarbonate or potassium bicarbonate or a mixture thereof.

Optionally, the alkali metal bicarbonate ingredient of an invention fungicide composition can be generated in situ in an aqueous medium. Thus, when urea is employed as the slow-release source of ammonia, it hydrolyzes to generate ammonia and bicarbonate ions. The net product result is the formation of ammonium bicarbonate in situ and the release of ammonia.

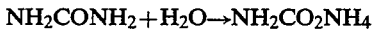
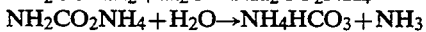

The alkali metal bicarbonate formation in situ can be accomplished by employing a urea acid salt such as urea hydrochloride, in combination with an alkali metal carbonate such as potassium carbonate. The hydrochloride and carbonate react to form a bicarbonate salt in situ.

The optional carbonate salt ingredient of an invention fungicide composition is selected from sodium carbonate, potassium carbonate, ammonium carbonate, lithium carbonate, and any mixture thereof. The carbonate salt serves to catalyze the hydrolysis of the ammonia releasing amide. An additional or alternative means of increasing the ammonia release rate is by utilizing an enzyme such as urease to catalyze the amide hydrolysis.

The spreader-sticker ingredient can consist of one or more components which function as a surfactant or a thickening agent.

Surfactants suitable for aqueous fungicide formulations are listed in publications such as U.S. Pat. No. 3,541,213. One type of surfactant is an alkali metal or ammonium salt of a $C_8$–$C_{22}$ aliphatic-containing carboxylate, sulfonate, sulfate or phosphate.

Illustrative of other surfactant types are dioctyl sodium sulfosuccinate, cetyltrimethyl-ammonium bromide; sodium lauryl sulfate; sodium dodecylbenzenesulfonate; ammonium lignosulfonate; condensation products of ethylene oxide with fatty alcohols, amines or alkylphenols; partial esters of fatty acids and hexitol anhydrides; and the like.

Thickening agents are illustrated by water-soluble polymers which exhibit pseudoplastic properties in an aqueous medium such as gum arabic, gum karaya, gum tragacanth, guar gum, locust bean gum, xanthan gum, carrageenan, alginate salt, casein, dextran, pectin, agar, 2-hydroxyethyl starch, 2-aminoethyl starch, 2-hydroxyethyl cellulose, methyl cellulose, carboxymethyl cellulose salt, cellulose sulfate salt, polyacrylamide, methyl vinyl ether/maleic anhydride copolymer, styrene/maleic anhydride copolymer, ethylene/maleic anhydride copolymer, the corresponding alkali metal salts of the maleic anhydride copolymers, alkali metal salts of poly(meth)acrylate, and the like.

Many of the water-soluble polymers are large volume commercial products. Sodium carboxymethyl cellulose (CMC) is available in powder or granular form having a particle size of 50–200 microns. CMC is available in a degree of substitution (DS) range of 0.38–1.4.

Oils which can be employed as a spreader-sticker ingredient in an invention fungicide composition include Orchex 796, Volck Oil #70, Sunoco Oil No. 7E, castor oil, corn oil, and similar nonphytotoxic spray oils of vegetable, animal or mineral origin commonly used in agricultural applications.

The ingredients in an invention fungicide composition can be selected to include nitrogen, phosphorus and potassium elements in a ratio that qualifies the composition to function as a fertilizer in addition to its function as a fungicide, when applied to cultivated crops. A typical ratio is 10–15–10. Besides nitrogen, phosphorus and potassium, an invention fungicidal fertilizer composition can contain trace elements, and other essential elements as exemplified by sulfur as contained in a compound such as sodium bisulfite or thiourea.

For purposes of this additional embodiment, the present invention provides a fungicidal fertilizer composition consisting of a dry blend formulation adapted for in situ generation of ammonium bicarbonate which comprises (1) between about 5–80 weight percent of an ingredient selected from water-soluble organic amides which slow-release ammonia under aqueous alkaline pH conditions at ambient temperatures; (2) between about 10–80 weight percent of an ingredient selected from alkali metal bicarbonates; (3) between about 0–30 weight percent of an ingredient selected from alkali metal and ammonium carbonates; (4) between about 0.5–20 weight percent of a spreader-sticker ingredient; and (5) between about 10–60 weight percent of an ingredient selected from phosphorus-containing compounds; based on the composition weight; wherein the composition ingredients have a formulated ratio of nitrogen, phosphorus and potassium elements.

In a further embodiment this invention provides an aqueous fungicidal fertilizer formulation adapted for in situ generation of ammonium bicarbonate under cultivated plant application conditions, which contains ingredients comprising (1) between about 0.2–5 weight percent of water-soluble organic amide which slow-releases ammonium under aqueous alkaline pH conditions at ambient temperature; (2) between about 0.5–5 weight percent of alkali metal bicarbonate; (3) between about 0–2 weight percent of alkali metal or ammonium carbonate; (4) between about 0.02–1.5 weight percent of a spreader-sticker ingredient; and (5) between about 0.5–4 weight percent of an ingredient selected from phosphorus-containing compounds; based on the formulation weight; wherein the composition ingredients have a formulated ratio of nitrogen, phosphorus and potassium elements.

An invention fungicide composition can include one or more other biologically active ingredients, such as those which exhibit herbicidal, insecticidal or plant growth regulating activity.

A fungicide composition of the present invention has a novel combination of properties for the practice of fungus control in agricultural and horticultural applications.

The multiple bicarbonate ingredients exhibit fungicidal properties, and the efficiency of any additionally included organic pesticide ingredient usually is enhanced by the presence of the bicarbonate ingredients. A lesser quantity of optional pesticide ingredient can be employed to achieve a desired degree of pest control.

A present invention fungicide composition can be formulated to exhibit no phytotoxicity, or to minimize the toxic effects of salt stress on plants by the bicarbonate ingredients.

A present invention fungicide composition provides particular advantage for the control of infectious phytopathogenic fungi which thrive under acidic soil conditions.

All of the invention fungicide composition ingredients are biocompatible when the composition is applied in an agricultural environment. The organic amide, bicarbonate and spreader-sticker ingredients are all harmless to animals and humans.

A significant feature of a present invention dry blend fungicide composition is the presence of a spreader-sticker ingredient when the fungicide composition is applied to plant foliage as a water-diluted solution. An applied aqueous solution forms an adherent coating of ingredients on plant foliage or fruit. A surfactant type ingredient aids in spreading and sticking the fungicide composition ingredients to the foliage or fruit to which it is applied. A hydrophilic polymer type ingredient increases the amount of aqueous fungicide composition which adheres to the plant surfaces because of its static high apparent viscosity. During a spraying procedure, the hydrophilic polymer ingredient contributes a low pseudoplastic viscosity to the spray solution, which facilitates the spraying action. After spraying, the applied coating resists drifting under wind conditions, and exhibits humectant properties in addition to enhanced fungicidal activity.

Another important advantage of a preferred invention fungicide composition derives from the water-solubility of the main ingredients. A coating of an invention fungicide composition on plant foliage or fruit can be removed readily by water-washing.

A unique feature of a present invention fungicide composition is the in situ generation of ammonium bicarbonate when the formulation has been applied to pre-harvest or post-harvest crops. Under conditions of ambient temperature and moisture, the organic amide releases ammonium ions over a sustained period of about 5–20 days after application of the fungicide composition. The slow-released ammonia and/or ammonium bicarbonate enhance the direct fungicidal activity of the other bicarbonates in the composition. The prolonged presence of ammonium bicarbonate on plant foliage or in soil provides an exceptional fungal control activity, as compared to an equivalent quantity or alkali metal bicarbonate in the absence of slow-release ammonium bicarbonate.

The following examples are further illustrative of the present invention. The components and specific ingredients are presented as being typical, and various modifications can be derived in view of the foregoing disclosure within the scope of the invention.

EXAMPLE I

This Example illustrates the preparation of in situ generating ammonium bicarbonate fungicide compositions in accordance with the present invention.

|  | weight percent | | | |
| --- | --- | --- | --- | --- |
| Urea | 32.0 | 40.0 | 20.0 | 0.0 |
| Dimethylolurea | 0.0 | 0.0 | 0.0 | 20.0 |
| Potassium bicarbonate | 36.5 | 41.0 | 40.0 | 0.0 |
| Sodium bicarbonate | 0.0 | 0.0 | 20.0 | 54.0 |
| Potassium carbonate | 14.0 | 18.0 | 0.0 | 0.0 |
| Sodium carbonate | 0.0 | 0.0 | 0.0 | 10.0 |
| Dioctyl sodium sulfosuccinate | 17.0 | 0.0 | 0.0 | 0.0 |
| Sodium lauryl sulfate | 0.0 | 0.0 | 18.0 | 12.0 |
| Magnesium oxide | 0.05 | 1.0 | 2.0 | 4.0 |

Each of the above blended compositions is dispersed in water to provide an aqueous formulation having a content of 0.5 weight percent of the urea or dimethylourea ingredient which slow-releases ammonia and/or ammonium bicarbonate under the alkaline pH conditions of the aqueous medium.

Test plots are established in a rice field. Each aqueous formulation is applied to a test plot at weekly intervals at a rate of 1000 liters per hectare.

After three months, the sprayed plots are healthy, and the untreated plots are damaged by rice blast fungus (*Pericularia oryzae*) and produce a lower yield of rice.

Under similar test conditions, test plots with formulations not containing the urea or dimethylolurea ingredient exhibit a slower growth rate, and minor traces of rice blast fungus are evident.

EXAMPLE II

This Example illustrates the preparation and application of a fungicide composition in accordance with the present invention.

A water-dispersible powder composition is prepared from the following weight percent ingredients:

| | |
| --- | --- |
| urea | 50 |
| sodium bicarbonate | 30 |
| potassium carbonate | 15 |

| | |
|---|---|
| guar gum | 1 |
| diocyl sodium sulfosuccinate | 2 |
| ultrafine silica | 2 |

The ingredients are blended and jet mill micronized to an average particle size of about 20 microns.

Test plots are established in a field planting of cantaloupe, and the crop is inoculated with powdery mildew fungus (*Erysiphe cichoracearum*).

The test plots are sprayed with an aqueous dispersion of the powder composition. The urea content of the aqueous solution is 0.3 weight percent.

After a month, the treated plants in the test plots are healthy and growing rapidly. The untreated plants are damaged by powdery mildew, and are slow growing.

EXAMPLE III

This Example illustrates the preparation of a fungicide powder formulation for disease prevention in accordance with the present invention.

A blend of the following weight percent ingredients is prepared:

| | |
|---|---|
| cyanuric acid | 20 |
| sodium bicarbonate | 30 |
| potassium bicarbonate | 15 |
| sodium stearate | 25 |
| xanthan gum | 10 |

The formulated concentrated powder is diluted with water by the dispersion of 2 parts of the powder blend into 100 parts of water. The resulting solution is sprayed onto ornamental plant foliage where it forms an adherent coating on the foliage surfaces, and prevents fungal disease infection of the plants.

EXAMPLE IV

This example illustrates the preparation of a fungicide-fertilizer composition.

A blend of the following weight ratio of ingredients is prepared:

| | Parts |
|---|---|
| melamine | 20 |
| urea clathrate[(1)] | 40 |
| potassium oleate | 2 |
| $KHCO_3$ | 25 |
| $Na_2CO_3$ | 5 |
| $K_3PO_4$ | 10 |

[(1)]Urea and occluded dodecanol containing an average of 7 moles of ethylene oxide.

Granules are prepared by tumbling the blend, spraying added water to form tacky solids, and then drying the granulated product.

The composition is used in granule form for application to soil, or the composition is dispersed in water for spray application to plant foliage.

(1) Urea and occluded dodecanol containing an average of 7 moles of ethylene oxide.

What is claimed is:

1. A fungicide composition consisting of a dry blend formulation adapted for in situ generation of ammonium bicarbonate which comprises (1) between about 5–80 weight percent of an ingredient selected from water-soluble organic amides which slow-release ammonia under aqueous alkaline pH conditions at ambient temperatures; (2) between about 10–80 weight percent of an ingredient selected from alkali metal bicarbonates; (3) between about 0–30 weight percent of an ingredient selected from alkali metal and ammonium carbonates; and (4) between about 0.5–20 weight percent of a spreader-sticker ingredient; all weights based on the composition weight.

2. A fungicide composition in accordance with claim 1 wherein the organic amide is urea or urea clathrate.

3. A fungicide composition in accordance with claim 1 wherein the organic amide is alkali metal carbamate.

4. A fungicide composition in accordance with claim 1 wherein the organic amide is biuret or triuret.

5. A fungicide composition in accordance with claim 1 wherein the organic amide is cyanuric acid.

6. A fungicide composition in accordance with claim 1 wherein the organic amide is a urea-formaldehyde adduct.

7. A fungicide composition in accordance with claim 1 wherein the spreader-sticker ingredient is a cationic, anionic or nonionic surfactant.

8. A fungicide composition in accordance with claim 1 wherein the spreader-sticker ingredient is an alkali metal or ammonium salt of a $C_2$–$C_{22}$ aliphatic-containing carboxylate, sulfonate, sulfate or phosphate.

9. A fungicide composition in accordance with claim 1 wherein the spreader-sticker ingredient is a hydrocolloid gum.

10. A fungicide composition in accordance with claim 1 wherein the spreader-sticker ingredient is a cellulosic derivative.

11. A fungicide composition in accordance with claim 1 wherein the spreader-sticker ingredient is a starch derivative.

12. A fungicide composition in accordance with claim 1 wherein the spreader-sticker ingredient is a polyacrylamide derivative.

13. A fungicide composition in accordance with claim 1 wherein the spreader-sticker ingredient is a nonphytotoxic aliphatic or triglyceride spray oil.

14. A fungicide composition in accordance with claim 1 wherein the ingredients comprise (1) urea; (2) sodium or potassium bicarbonate or a mixture thereof; (3) sodium or potassium or ammonium carbonate or a mixture thereof; and (4) an alkali metal or ammonium salt of a $C_8$–$C_{22}$ aliphatic-containing carboxylate, sulfonate, sulfate or phosphate.

15. An aqueous fungicidal formulation adapted for in situ generation of ammonium bicarbonate under cultivated plant application conditions, which contains ingredients comprising (1) between about 0.1–5 weight percent of water-soluble organic amide which slow-releases ammonia under aqueous alkaline pH conditions at ambient temperature; (2) between about 0.2–5 weight percent of alkali metal bicarbonate; (3) between about 0–2 weight percent of alkali metal or ammonium carbonate; and (4) between about 0.02–1.5 percent of a spreader-sticker ingredient; all weights based on the formulation weight.

16. A fungicide formulation in accordance with claim 15 wherein the organic amide is urea or urea clathrate.

17. A fungicide formulation in accordance with claim 15 wherein the spreader-sticker ingredient is a cationic, anionic or nonionic surfactant.

18. A fungicide formulation in accordance with claim 15 wherein the spreader-sticker ingredient is a nonphytotoxic aliphatic or triglyceride spray oil.

19. A fungicide formulation in accordance with claim 15 wherein the ingredients comprise (1) urea; (2) sodium or potassium bicarbonate or a mixture thereof; (3) sodium or potassium or ammonium carbonate or a mixture thereof; and (4) an alkali metal or ammonium salt of a $C_8$–$C_{22}$ aliphatic-containing carboxylate, sulfonate, sulfate or phosphate.

20. A fungicide composition in accordance with claim 15 which has an aqueous medium pH between about 7.5–10.5.

21. A method of controlling fungal disease in cultivated plants which comprises applying a fungicidally effective amount of an aqueous formulation in accordance with claim 15 to the plant foliage to prevent or eradicate fungal infections.

22. A method in accordance with claim 21 wherein the aqueous formulation is applied by spraying.

* * * * *